United States Patent [19]

Thakkar

[11] 4,278,603

[45] Jul. 14, 1981

[54] NOVEL POLYMORPHIC CRYSTALLINE FORM OF DIBENZOPYRANONE

[75] Inventor: Arvind L. Thakkar, Indianapolis, Ind.

[73] Assignee: Eli Lilly and Company, Indianapolis, Ind.

[21] Appl. No.: 822,471

[22] Filed: Aug. 8, 1977

Related U.S. Application Data

[63] Continuation of Ser. No. 707,786, Jul. 22, 1976, abandoned, which is a continuation-in-part of Ser. No. 628,521, Dec. 8, 1975, abandoned, which is a continuation-in-part of Ser. No. 504,391, Sep. 11, 1974, abandoned, which is a continuation-in-part of Ser. No. 413,011, Nov. 5, 1973, abandoned.

[51] Int. Cl.³ .......................................... C07D 311/80
[52] U.S. Cl. .................................. 260/345.3; 424/283
[58] Field of Search ...................................... 260/345.3

[56] References Cited

U.S. PATENT DOCUMENTS

3,507,885  4/1970  Fahrenholtz ..................... 260/345.3

FOREIGN PATENT DOCUMENTS

821720  4/1975  Belgium .............................. 260/345.3

OTHER PUBLICATIONS

Fahrenholtz et al., JACS, 89, 5934 (1967).
Fahrenholtz et al., JACS, 88, 2079 (1966).

*Primary Examiner*—Nicky Chan
*Attorney, Agent, or Firm*—James L. Rowe; Arthur R. Whale

[57] ABSTRACT

Stable polymorphic crystalline form of trans-dl-1-hydroxy-3-(1',1'-dimethylheptyl)-6,6-dimethyl-6,6a,7,8,-10,10a-hexahydro-9H-dibenzo[b,d]pyran-9-one, capable of producing significant blood levels in mammals for long periods of time after oral administration of the drug.

1 Claim, No Drawings

NOVEL POLYMORPHIC CRYSTALLINE FORM OF DIBENZOPYRANONE

CROSS-REFERENCE

This is a continuation of application Ser. No. 707,786, filed July 22, 1976, now abandoned, which in turn is a continuation-in-part of my copending application Ser. No. 628,521 filed Dec. 8, 1975, now abandoned which was in turn a continuation-in-part of my then copending application Ser. No. 504,391, filed Sept. 11, 1974 now abandoned which was in turn a continuation-in-part of my then copending application Ser. No. 413,011 filed Nov. 5, 1973, now abandoned.

BACKGROUND OF THE INVENTION

1-Hydroxy-3-alkyl-6,6-dimethyl-6,6a,7,8,10,10a-hexahydro-9H-dibenzo[b,d]pyran-9-ones, their ethers and esters are disclosed in U.S. Pat. No. 3,507,885 as intermediates for the preparation of $\Delta^8$ or $\Delta^9$-tetrahydrocannabinols ($\Delta^8$ or $\Delta^9$-THC). No utility other than as intermediates was disclosed for these compounds until Archer, U.S. Pat. No. 3,928,598 issued Dec. 23, 1975, filed Nov. 5, 1973 disclosed their use as anti-anxiety and/or anti-depressant drugs and as sedative and/or analgesic drugs.

$\Delta^9$-THC and other structurally related dibenzopyrans, either obtainable from natural sources or from various synthetic procedures, are known to be extremely insoluble in aqueous media. Consequently, there has been a continuing problem in determining the pharmacological activities of this type of compound when administered by the oral route since there exists a high degree of uncertainty as to the amount of absorption of these extremely insoluble substances after oral administration. The uncertainty as to the degree of absorption of these compounds is further complicated by a tendency of the compounds to exist in the solid state in several polymorphic forms.

SUMMARY OF THE INVENTION

This invention provides a novel, stable polymorphic form of trans-dl-1-hydroxy-3-(1'1'-dimethylheptyl)-6,6-dimethyl-6,6a,7,8,10,10a-hexahydro-9H-dibenzo[b,d]-pyran-9-one. The racemate has the following physical characteristics: shows birefringence under a polarizing microscope, shows endotherms under differential thermal analysis at 137° C., 153° C. and 160° C. and has the following x-ray powder diffraction pattern using filtered chromium radiation having a wave-length at 2.2896Å.

| "d" in A. | I/I° |
|---|---|
| 14.5 | 100 |
| 10.5 | 30 |
| 8.4 | 60 |
| 7.2 | 40 |
| 6.50 | 20 |
| 5.90 | 30 |
| 4.85 | 60 |
| 4.10 | 05 |
| 3.90 | 40 |
| 3.35 | 30 |

My novel polymorphic crystalline form is prepared as follows: An ethanol solution of a physiologically unavailable, non-orally-absorbable polymorphic crystalline form of trans-dl-1-hydroxy-3-(1'1'-dimethylheptyl)-6,6a,7,8,10,10a-hexahydro-9H-dibenzo[b,d]pyran-9-one, incapable of producing significant blood levels of drug after oral administration to mammals and prepared by recrystallization from either acetone or hexane, is added with very rapid stirring to a large quantity of water. The dibenzopyranone, being practically insoluble in water, precipitates immediately. Stirring is continued for a short period of time, and then the precipitated drug of the desired polymorphic form having the above physical characteristics is collected by filtration and dried. Alternatively, the ethanol solution can be diluted with a relatively large volume of water with rapid stirring to prepare my novel polymorphic forms.

Crystal growth retarding agents such as polyvinylpyrrolidone, methyl cellulose, sodium alginate, dextran, gelatin, acacia, etc. may be employed to prevent the transformation of my novel polymorphic form into the more usual crystalline forms as are obtained by recrystallizing the drug from acetone or hexane. If it is desirable to use such agents, they should be added to the water prior to the addition of the ethanol solution of the drug thereto.

Alternatively, my novel crystalline form of trans-dl-1-hydroxy-3-(1',1'-dimethylheptyl)-6,6-dimethyl-6,6a,7,8,10,10a-hexahydro-9H-dibenzo[b,d]pyran-9-one can be prepared by forming a solution of the drug in ethanol and then removing the solvent by evaporation at a temperature in the range 25°–55° C. It is preferred to use a rotary evaporator in this process, and the evaporation temperature is readily maintained in the desired temperature range by use of a water bath.

A pharmaceutical formulation containing one part of trans-dl-1-hydroxy-3-(1',1'-dimethylheptyl)-6,6-dimethyl-6,6a,7,8,10,10a-hexahydro-9H-dibenzo[b,d]pyran-9-one in a relatively absorbable polymorphic form prepared as indicated above was thoroughly mixed with nine parts of cornstarch, and the mixture placed in telescoping gelatin capsules and tested for absorption in two dogs. The compound in capsule form was administered by the oral route. Expected side effects observed with other orally absorbable forms, or with parenteral injection, of the drug were observed, such side effects including head nod, body sway and ataxia. The starch preparation in capsules was retested two weeks and again ten weeks later with identical results, indicating that the polymorphic form of this invention is stable in the presence of starch. Other polymorphic forms of trans-dl-1-hydroxy-3-(1',1'-dimethylheptyl)-6,6-dimethyl-6,6a,7, 8,10,10a-hexahydro-9H-dibenzo[b,d]pyran-9-one, even though active in solution or soon after mixing with starch, apparently slowly recrystallize or undergo polymorphic transformation so as to affect adversely their bioavailability.

Pharmaceutical formulations containing my novel polymorphic form of trans-dl-1-hydroxy-3-(1',1'-dimethylheptyl)-6,6-dimethyl-6,6a,7,8,10,10a-hexahydro-9H-dibenzo-[b,d]pyran-9-one can be used to treat anxiety or depression or to provide analgesia or sedation as set forth in U.S. Pat. Nos. 3,944,673, 3,928,598 and 3,953,603.

This specification is further illustrated by the following specific example:

EXAMPLE 1

A solution of 1 g. of trans-dl-1-hydroxy-3-(1',1'-dimethylheptyl)-6,6-dimethyl-6,6a,7,8,10,10a-hexahydro-9H-dibenzo[b,d]pyran-9-one in 25 ml. of ethanol was added to 1 liter of water at about 25° C. with high speed stirring. The stirring was continued for about 4 hours after the ethanol solution had been added. Trans-dl-1-hydroxy-3-(1',1'-dimethylheptyl)-6,6-dimethyl-6,6a,7,8,10,10a-hexahydro-9H-dibenzo[b,d]pyran-9-one precipitated, and the precipitate was collected by filtration. The precipitated dibenzopyranone was in the polymorphic form having the characteristics set forth above for the trans racemate. The form thus prepared was microcrystalline with a particle size ranging from 2.2–26 microns with 50% by volume being less than 7.2 microns.

EXAMPLE 2

A solution was prepared at room temperature as in Example 1 containing 1 g. of 1-hydroxy-3-(1',1'-dimethylheptyl)-6,6-dimethyl-6,6a,7,8,10,10a-hexahydro-9H-dibenzo-[b,d]pyran-9-one in 25 ml. of ethanol. The solution was placed in a rotary evaporator which was in turn placed in a water-bath held in the range 25°–55° C.

The trans racemate which is converted to an absorbable polymorphic form is prepared as a mixture with the cis racemate by the procedure of Fahrenholtz et al., J. Am. Chem. Soc., 88, 2079 (1966), 89, 5934 (1967)—see also U.S. Pat. No. 3,507,885—using 5-(1',1'-dimethylheptyl) resorcinol in place of 5-n-pentyl resorcinol employed by Fahrenholtz et al.

The synthesis of the starting materials useful in the above examples is illustrated by the following preparations:

PREPARATION 1

Preparation of
1-hydroxy-3-(1',1'-dimethylheptyl)-6,6-dimethyl-6,6a,7,8,10,10a-hexahydro-9H-dibenzo[b,d]pyran-9-one.

A mixture containing 114 g. of 5-(1',1'-dimethylheptyl) resorcinol, 112 g. of diethyl 2-acetylglutarate and 74 g. of phosphorous oxychloride was stirred at ambient temperature for about ten days. The reaction mixture was then dissolved in ethyl acetate and the ethyl acetate layer washed several times with an equal volume of water until the water wash was neutral to litmus. The organic layer was separated and dried, and the solvent removed by evaporation in vacuo. The residue, comprising ethyl 7-(1',1'-dimethylheptyl)-5-hydroxy-4-methyl-2-oxy-2H-1-benzopyran-3-propionate formed in the above reaction, was purified by chromatography over 2 kg. of neutral alumina using chloroform as the eluant. 142 g. of purified product thus obtained, were dissolved in 300 ml. of DMSO (dimethylsulfoxide), and the solution added in dropwise fashion to a suspension of 33.6 g. of sodium hydride in 100 ml. of DMSO. After the addition had been completed, the reaction mixture was allowed to stand at ambient temperature overnight. Excess sodium hydride present was decomposed by the dropwise addition of ethanol. The reaction mixture was next carefully poured over a mixture of ice and 12 N aqueous hydrochloric acid. A solid resulted comprising 3-(1',1'-dimethylheptyl)-7,10-dihydro-1-hydroxy-6H-dibenzo[b,d]pyran-6,9(8H)-dione, which was collected by filtration. The solid filter cake was dissolved in methyl ethyl ketone and the resulting solution washed with 5 percent aqueous sodium bicarbonate followed by saturated aqueous sodium chloride. The organic layer was dried, and the solvent removed by evaporation in vacuo. Trituration of the crude residue with anhydrous ether followed by filtration (the filtrate being discarded) yielded about 92.6 g. of a light yellow solid. 3-(1',1'-Dimethylheptyl)-7,10-dihydro-1-hydroxy-6H-dibenzo[b,d]pyran-6,9(8H)-dione thus obtained was used in its semi-purified state. A solution of 2.3 g. of the above product in 125 ml. of benzene also containing 2.5 ml. of ethylene glycol and 5 mg. of p-toluenesulfonic acid was heated overnight under reflux using a water collector. After cooling, the reaction mixture was poured into 5 percent aqueous sodium bicarbonate. The organic layer was separated, washed with water and then dried. Removal of the organic solvent in vacuo yielded 2.5 g. of 3-(1',1'-dimethyl-heptyl)-7,8-dihydro-1-hydroxyspiro[9H-dibenzo[b,d]pyran-9,2'-[1,3]-dioxolan]-6(10H)-one. This product was also used without purification.

A solution of the product in 50 ml. of anhydrous ether was added dropwise to 46 ml. of a 2.8 M methyl Grignard Reagent in anhydrous ether. After the addition had been completed, the reaction mixture was refluxed overnight, cooled, and then carefully poured into an ice and 6N aqueous hydrochloric acid mixture. Evaporation of the ether by heating on a steam bath yielded a light yellow precipitate which was collected by filtration. The solid material was washed several times with ether to give 1.64 g. of a light yellow solid comprising dl-3-(1',1'-dimethylheptyl)-6,6a,7,8-tetrahydro-1-hydroxy-6,6-dimethyl-9H-dibenzo[b,d]pyran-9-one; MP=194°–196° C.

Rf=0.26 (silica gel, 20% ethyl acetate:benzene): UV-(ethanol).

$\lambda_{max}$ 207/230/323 m$\mu$ ($\epsilon$=25,600/13,200/23,200); IR(Chloroform) 6.1$\mu$ (C=O); NMR (CDCl$_3$).

$\delta$7.4 (d/J=2 cps/1H/H$_{10}$), $\delta$6.46/6.26(2d/J=2 cps/2H/H$_2$ and H$_4$), $\delta$1.21(s/6H/gem dimethyl at C-1') and $\delta$9.83 ppm (t/3H/-$\alpha$-methyl); molecular ion; m/e=370.

A solution of 1.5 g. of dl-3-(1',1'-dimethylheptyl)-6,6a,7,8-tetrahydro-1-hydroxy-6,6-dimethyl-9H-dibenzo[b,d]-pyran-9-one in 50 ml. of anhydrous tetrahydrofuran (THF) was added dropwise to a solution of lithium metal in liquid ammonia at $-80°$ C. Excess lithium metal was added in chunks to the solution as the blue color, indicating free dissolved lithium, disappeared. After the addition was complete, ammonium chloride was added to react with any excess lithium metal still present. The mixture was then allowed to warm to room temperature in a nitrogen atmosphere during which process the ammonia evaporated. The reaction mixture was then acidified with 1N aqueous hydrochloric acid, and the organic constituents extracted with ethyl acetate. The ethyl acetate extracts were combined, washed with water and dried. Evaporation of the ethyl acetate under reduced pressure yielded 1.4 g. of crude trans-dl-3-(1',1'-dimethylheptyl)-6,6a,7,8,10,10a-hexahydro-1-hydroxy-6,6-dimethyl-9H-dibenzo[b,d]-pyran-9-one. The crude product was chromatographed over 50 g. of silica gel from benzene solution and the desired product was eluted in 20 ml. fractions with a benzene eluant containing 2 percent ethyl acetate. Fractions 200–240 contained 808 mg. of a white crystalline solid comprising purified trans-dl-3-(1',1'-dimethylheptyl)-6,6a,7,8,10,10a-hexahydro-1-hydroxy-6,6-dimethyl-9H-dibenzo-[b,d]pyran-9-one. The purified compound melted at 159°–160° C. after recrystallization from an ethyl acetate-hexane solvent mixture. R$_f$=0.45 (silica gel, 20% ethyl acetate benzene).

UV(ethanol) $\lambda$max 207/280 m$\mu$ ($\epsilon$=47,000/250); IR(CHCl$_3$) 5.85.

μ(C=O); NMR (CDCl$_3$) δ7.75(s/1H/exchanges with D$_2$O), δ6.36/6.34 (2d/J=2 cps/2H/H$_2$ and H$_4$), δ4.15(d broad/J=14,3 cps/1H/H$_{10α}$), δ3.08–0.7 (multiplet/32H), especially δ1.47/1.13 (2s/each 3H/6α and 6β CH$_3$), δ1.21 (s/6H/gem-dimethyl at C-1') and δ0.83 ppm (t/3H/ω-methyl); molecular ion, m/e 372.

Anal. Calcd. for C$_{24}$H$_{36}$O$_3$: C, 77.38; H, 9.74; O, 12.88. Found: C, 77.59; H, 9.68; O, 12.99.

I claim:

1. A polymorphic form of dl-1-hydroxy-3-(1',1'-dimethylheptyl)-6,6-dimethyl-6,6a,7,8,10,10a-hexahydro-9H-dibenzo[b,d]pyran-9-one, capable of producing significant blood levels in mammals for long periods of time after oral administration of the drug, prepared by adding an ethanol solution of a non-orally absorbable polymorphic form of the said pyran-9-one recrystallized from either acetone or hexane and incapable of producing significant blood levels of drug after oral administration in mammals, with stirring to a large quantity of water.

* * * * *